(12) United States Patent
Hruby et al.

(10) Patent No.: US 10,653,743 B2
(45) Date of Patent: *May 19, 2020

(54) METHODS FOR THE TREATMENT OF DEPRESSION AND ANXIETY BY A MELANOCORTIN 5 RECEPTOR ANTAGONIST, PG-20N

(71) Applicants: ARIZONA BOARD OF REGENTS ON BEHALF OF THE UNIVERSITY OF ARIZONA, Tucson, AZ (US); THE TEXAS A&M UNIVERSITY SYSTEM, College Station, TX (US)

(72) Inventors: Victor J. Hruby, Tucson, AZ (US); Minying Cai, Tucson, AZ (US); Caurnel Morgan, College Station, TX (US)

(73) Assignees: ARIZONA BOARD OF REGENTS ON BEHALF OF THE UNIVERSITY OF ARIZONA, Tucson, AZ (US); THE TEXAS A&M UNIVERSITY SYSTEM, College Station, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/768,267

(22) PCT Filed: Oct. 17, 2016

(86) PCT No.: PCT/US2016/057329
§ 371 (c)(1),
(2) Date: Apr. 13, 2018

(87) PCT Pub. No.: WO2017/066754
PCT Pub. Date: Apr. 20, 2017

(65) Prior Publication Data
US 2018/0311304 A1 Nov. 1, 2018

Related U.S. Application Data
(60) Provisional application No. 62/242,228, filed on Oct. 15, 2015.

(51) Int. Cl.
*A61K 38/00* (2006.01)
*A61K 49/00* (2006.01)
(Continued)

(52) U.S. Cl.
CPC ............ *A61K 38/08* (2013.01); *A61K 9/0019* (2013.01); *A61K 9/0053* (2013.01); *A61K 38/10* (2013.01); *A61K 38/12* (2013.01); *A61K 38/177* (2013.01); *A61K 47/24* (2013.01); *C07D 473/00* (2013.01); *C07K 7/06* (2013.01); *C07K 7/08* (2013.01); *C07K 14/68* (2013.01); *C07K 14/685* (2013.01); *C07K 14/723* (2013.01); *G01N 2333/72* (2013.01); *G01N 2500/10* (2013.01)

(58) Field of Classification Search
CPC ........ C07K 14/723; C07K 14/68; C07K 7/08; C07K 7/64; C07K 14/685; C07K 7/06; C07K 14/665; A61K 38/10; A61K 38/12; A61K 38/00; A61K 38/08; A61K 47/24; A61K 38/07; A61K 38/177; A61K 38/22; A61K 9/0019; G01N 2333/726
See application file for complete search history.

(56) References Cited

U.S. PATENT DOCUMENTS 6,054,556 A * 4/2000 Huby ................... C07K 14/685
530/312
7,754,691 B1 * 7/2010 Sharma ................ C07K 5/1002
514/10.7
(Continued)

FOREIGN PATENT DOCUMENTS

WO WO2005079574 A1 9/2005
WO WO2014136118 A1 9/2014
(Continued)

OTHER PUBLICATIONS

Stankova, PhD. dissertation, The Univeristy of Arizona, 2004.*
Liu et al. Endocrinology, 2007; 148:6631-5540.*
Grieco et al. Biochm. Biophy. Res. Comm. 2002; 292:1075-1080.*
Greico et al. "Design and Microwave-Assisted Synthesis of Novel Macrocyclic Peptides Active at Melanocortin Receptors: Discovery of Potent and Selective hMC5R Receptor Antagonists," J. Med. Chem., May 8, 2008 (May 8, 2008), vol. 51, vol. 9, pp. 2701-2707 and Supporting Information.
(Continued)

*Primary Examiner* — Chang-Yu Wang
(74) *Attorney, Agent, or Firm* — Nguyen Tarbet

(57) ABSTRACT

Compositions and methods for treating a depressive disorder or an anxiety disorder in a subject in need of such treatment are described. A therapeutically effective amount of a composition comprising compound PG-20N in a pharmaceutically acceptable carrier is described. According to another embodiment, the subject disclosure features method of treating a depressive disorder or an anxiety disorder in a subject in need of such treatment. The method may comprise administering to the subject a therapeutically effective amount of a composition comprising PG-20N.

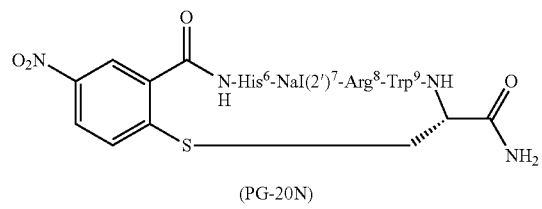

(PG-20N)

12 Claims, 3 Drawing Sheets
Specification includes a Sequence Listing.

(51) Int. Cl.

| | | |
|---|---|---|
| A61B 5/00 | (2006.01) | |
| A61K 35/30 | (2015.01) | |
| A61K 31/54 | (2006.01) | |
| C07K 7/08 | (2006.01) | |
| C07K 14/685 | (2006.01) | |
| A61K 38/08 | (2019.01) | |
| A61K 9/00 | (2006.01) | |
| A61K 38/10 | (2006.01) | |
| A61K 38/17 | (2006.01) | |
| C07K 14/68 | (2006.01) | |
| C07K 14/72 | (2006.01) | |
| A61K 38/12 | (2006.01) | |
| A61K 47/24 | (2006.01) | |
| C07K 7/06 | (2006.01) | |
| C07D 473/00 | (2006.01) | |

(56) References Cited

U.S. PATENT DOCUMENTS

| | | | | |
|---|---|---|---|---|
| 7,795,378 | B2 * | 9/2010 | Sharma | C07K 5/0806 530/300 |
| 9,458,195 | B2 * | 10/2016 | Dong | C07K 7/06 |
| 9,814,755 | B2 * | 11/2017 | Hruby | A61K 38/12 |
| 9,821,023 | B2 * | 11/2017 | Hruby | A61K 38/12 |
| 9,850,280 | B2 * | 12/2017 | Dong | C07K 7/06 |
| 2002/0143141 | A1 | 10/2002 | Chen et al. | |
| 2005/0124553 | A1 * | 6/2005 | Sharma | C07K 5/0806 514/180 |
| 2010/0129319 | A1 * | 5/2010 | Lindquist | A61K 31/00 424/85.2 |
| 2015/0037376 | A1 | 2/2015 | Seth et al. | |
| 2017/0020952 | A1 * | 1/2017 | Hruby | A61K 38/12 |
| 2017/0020953 | A1 * | 1/2017 | Hruby | A61K 38/12 |
| 2018/0319843 | A1 * | 11/2018 | Hruby | A61K 38/08 |

FOREIGN PATENT DOCUMENTS

| | | |
|---|---|---|
| WO | WO2017066754 A1 | 4/2017 |
| WO | WO2018074999 A1 | 4/2018 |

OTHER PUBLICATIONS

Mayorov et al. "Effects of Macrocycle Size and Rigidity on Melanocortin Receptor-I and Selectivity in Cyclic Lactam a-Melanocyte-Stimulating Hormone Analogs," Chem Bioi Drug Des., Jun. 9, 2006 (Jun. 9, 2006), vol. 67, No. 5, pp. 329-335.

Hruby. VJ et al. Approaches to the Rational Design of Selective Melanocortin Receptor Antagonists. Expert Opinion on Drug Discovery. May 2011 vol. 6. Issue 5. pages 543-557.p. 9. paragraph (4); p. 24. table 5.

* cited by examiner

METHODS FOR THE TREATMENT OF DEPRESSION AND ANXIETY BY A MELANOCORTIN 5 RECEPTOR ANTAGONIST, PG-20N

CROSS REFERENCE

This application claims priority to U.S. Provisional Patent Application No. 62/242,228, filed Oct. 15, 2015, the specification(s) of which is/are incorporated herein in their entirety by reference.

REFERENCE TO SEQUENCE LISTING

Applicant asserts that the information recorded in the form of an Annex C/ST.25 text file submitted under Rule 13ter.1(a), entitled UNIA_15_37_PCT1_Sequence_Listing_ST25, is identical to that forming part of the international application as filed. The content of the sequence listing is incorporated herein by reference in its entirety.

FIELD OF THE INVENTION

The present invention relates to compositions and methods for treating depression or anxiety, in particular, treating depression or anxiety with a selective melanocortin 5 receptor (MC5R) antagonist.

BACKGROUND OF THE INVENTION

Depression and anxiety contribute significantly to death and disability worldwide, and they frequently occur together. Although antidepressants are widely used to treat these disorders, they typically exert only modest therapeutic efficacy after weeks of administration. In addition, antidepressants can initially worsen symptoms in some patients, they have serious side effects, and as many as one-third of patients who take them are resistant to their therapeutic effects. One reason that all antidepressants approved by the U.S. Food and Drug Administration to treat depression and anxiety perform sub-optimally is that they all exert actions on just three of the many signaling systems found in the brain. Therefore, drugs that target different brain systems are highly sought for in the development of new antidepressants.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

According to one embodiment, the present invention features a composition for use in treating a depressive disorder or an anxiety disorder. The composition for use may comprise:

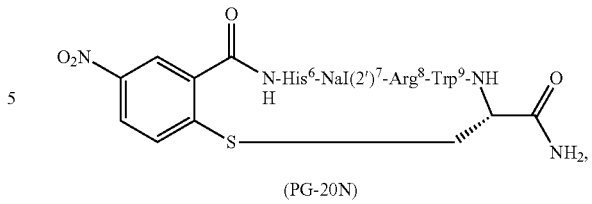

(PG-20N)

in a pharmaceutically acceptable carrier.

According to another embodiment, the subject disclosure features method of treating a depressive disorder or an anxiety disorder in a subject in need of such treatment. The method may comprise administering to the subject a therapeutically effective amount of a composition comprising:

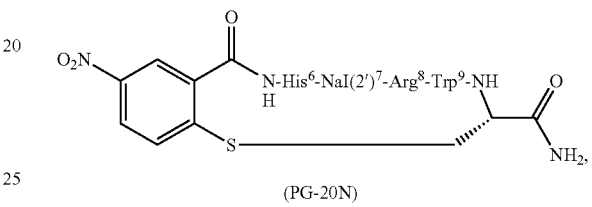

(PG-20N)

in a pharmaceutically acceptable carrier.

One of the unique and inventive technical features of the present invention is the PG-20N for use in treating the depressive disorder or anxiety disorder. Without wishing to limit the invention to any theory or mechanism, it is believed that the technical feature advantageously provides for a quicker and more potent clinical improvement than existing anti-depressants. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which:

FIG. 1A shows the results of the AFEC test in an anxiogenic environment, whereas FIG. 1B shows the results of the AFEC test in a non-anxiogenic home cage. As shown in FIG. 1C, the feed latency in the anxiogenic test cage is normalized to the latency in the non-anxiogenic home cage to generate the feed latency ratio. An elevated ratio is a second measure of anxiety that controls for drug effects on motor activity, olfaction, etc.

As shown in FIG. 2A, a reduction of the time spent investigating a reward cassette (containing graham cracker) in a non-anxiogenic environment is one parameter of anhedonia. FIG. 2B shows results from a blank investigation where a blank cassette (no graham cracker) is assessed as a negative control. Referring to FIG. 2C, the ratio of reward investigation to total investigation is then assessed as a control for drug effects on motor activity, olfaction, etc.

FIG. 3A shows central administration of melanocortin receptor agonist, NDP-α-MSH, elevated depression-related immobility. FIG. 3B shows non-selective melanocortin receptor antagonist, H-2784, reduced depression-related immobility. FIG. 3C shows PG-20N reduced depression-related immobility.

DESCRIPTION OF PREFERRED EMBODIMENTS

Before the present method is disclosed and described, it is to be understood that this invention is not limited to specific compositions and methods, as such may, of course, vary. It is also to be understood that the terminology used herein is for the purpose of describing particular embodiments only and is not intended to be limiting.

PG-20N is based on a cyclic lactam heptapeptide SHU9119, Ac-Nle$^4$-c[(Asp$^5$-His$^6$-DNal(2')$^7$-Arg$^8$-Trp$^9$-Lys$^{10}$]-NH$_2$, where in the core sequence "His$^6$-DNal(2')$^7$-Arg$^8$-Trp", the DNal(2') residue is replaced with its isomer LNal(2').

As used herein, "clinical improvement" may refer to a noticeable reduction in the symptoms of a disorder, or cessation thereof.

As defined herein, the term "antagonist" refers to compound that diminishes a response. The antagonist binds to the same site as the endogenous compound and diminishes or blocks the signal generated by the endogenous agent.

Figure 1A:
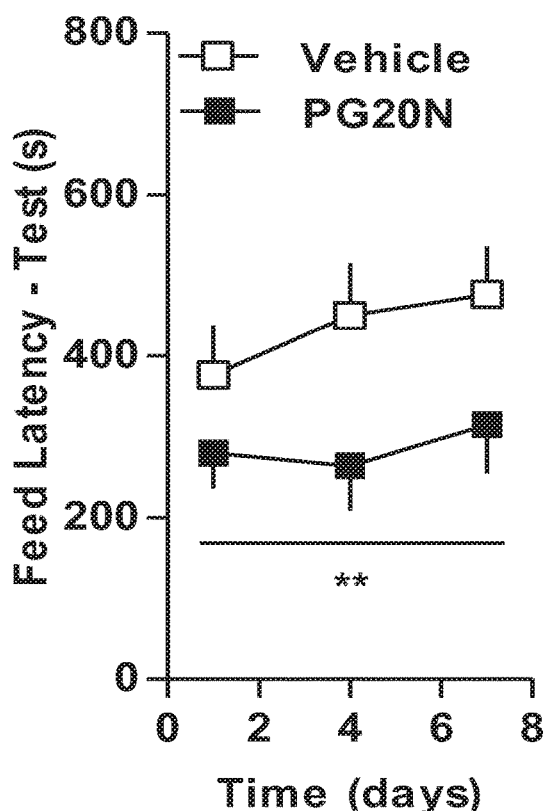
FIG. 1A-1C shows exemplary results from anxiety-related feeding/exploration conflict (AFEC) test. The AFEC test of the present invention is a version of the novelty-suppressed feeding (NSF) test, which is alternatively called the novelty-induced hypophagia (NIH) test. In all versions of the test, high latency to feed in an anxiogenic environment (e.g., new cage) is the parameter for anxious behavior.
Figure 1B:
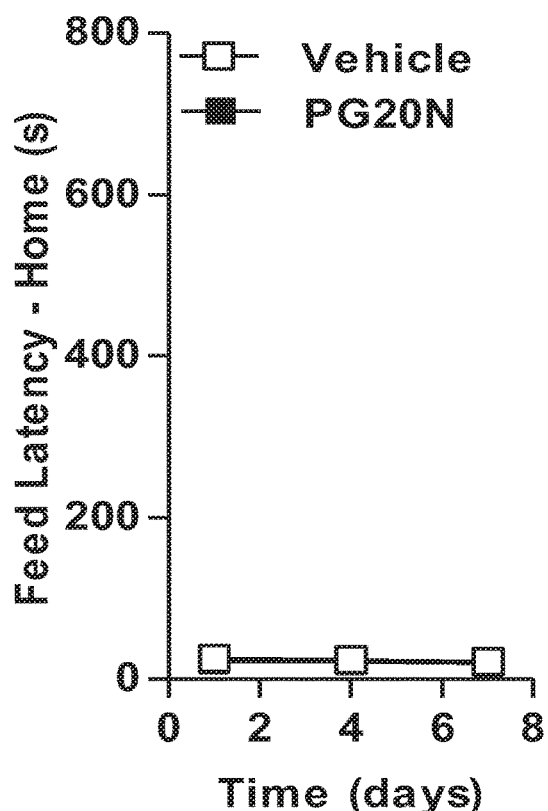
Figure 1C:
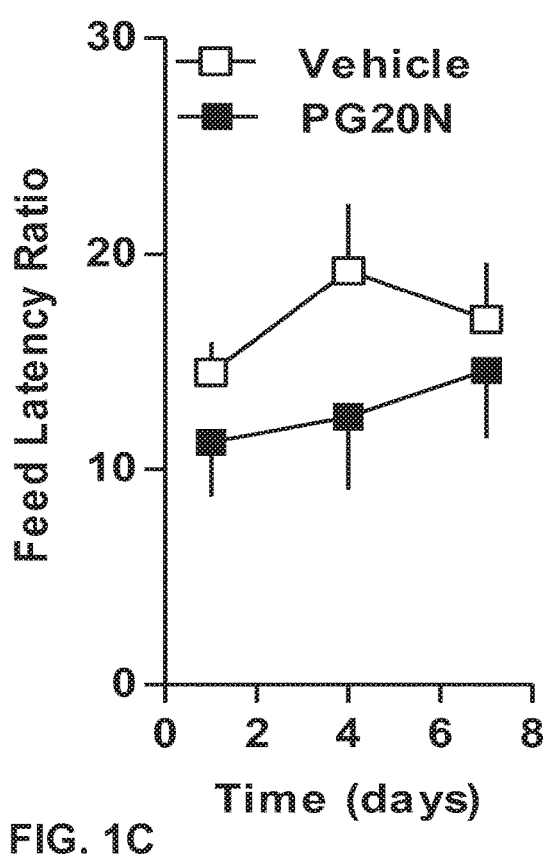
Figure 2A:
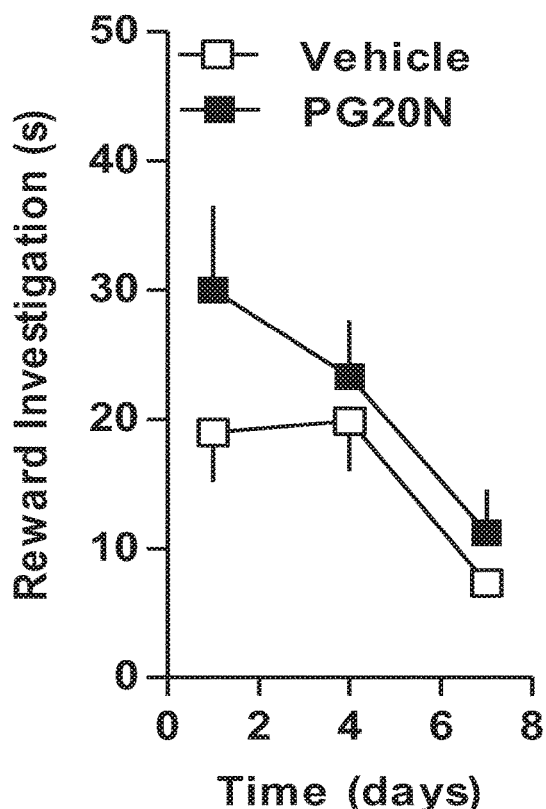
FIG. 2A-2C shows exemplary results from reward investigational preference (RIP) tests (depression-related anhedonia). The RIP test assesses depression-related anhedonia. Anhedonia is defined as the reduced ability to experience pleasure.
Figure 2B:
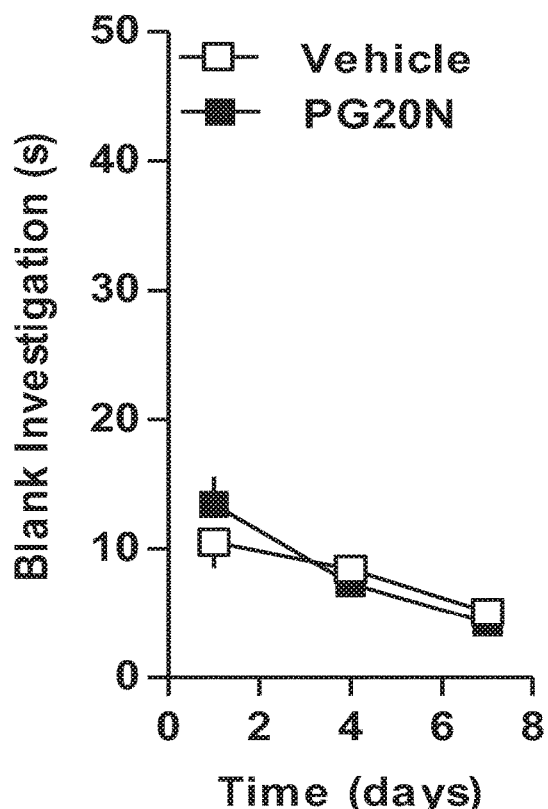
Figure 2C:
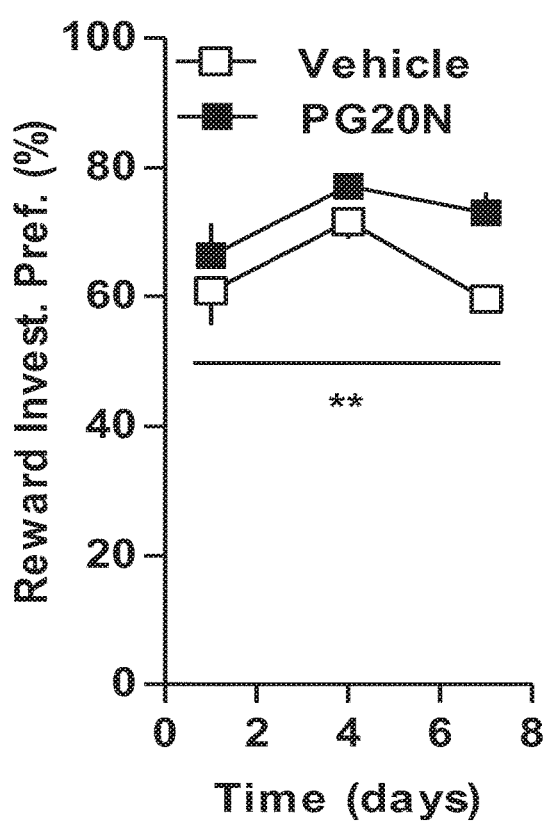
Figure 3A:
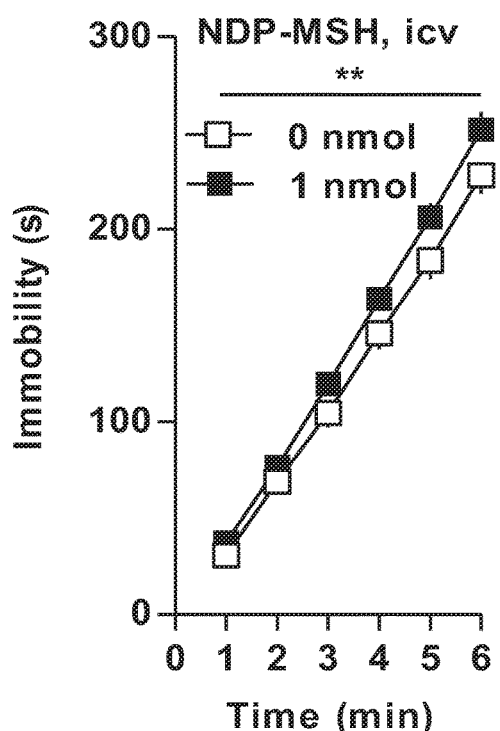
FIG. 3A-3C show exemplary results from tail suspension test. Male mice were injected intracerebroventricularly 1 h before assessment in the tail suspension test. The tail suspension test (TST) is a common test for a depression-related trait, psychomotor inhibition. A high level of immobility relates to depression.
Figure 3B:
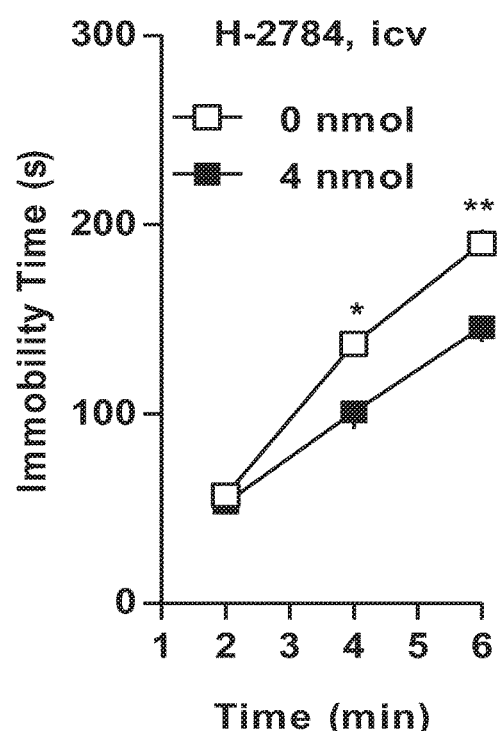
Figure 3C:
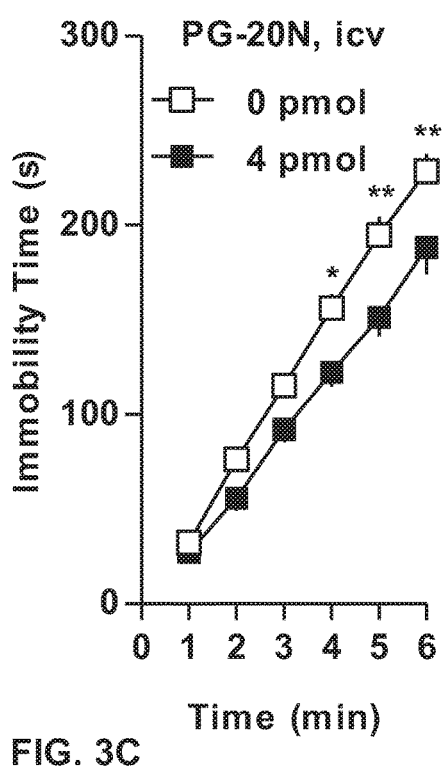

Referring now to FIGS. 1A-3C, the present invention may feature a method of treating a depressive disorder or an anxiety disorder in a subject in need of such treatment. According to one embodiment, the method may comprise administering to the subject a therapeutically effective amount of a composition comprising:

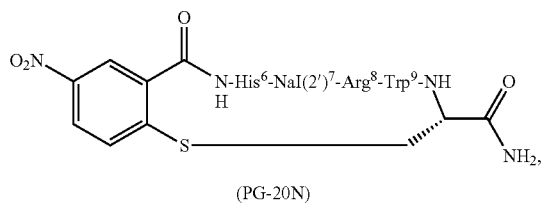

(PG-20N)

in a pharmaceutically acceptable carrier. In preferred embodiments, the composition is capable of treating the depressive disorder or the anxiety disorder such that clinical improvement is observed in about 1 to 14 days. For example, clinical improvement may be observed in about 1-7 days or about 7-14 days.

In one embodiment, the subject may be a mammal, such as a human. In another embodiment, the composition is administered in a dosage of about 0.001 mg/kg to 100 mg/kg of body weight. The composition may be administered once daily or twice daily; or the composition may be administered at least once daily, at least once every other day, or at least once weekly. In a further embodiment, the composition may be administered intravenously, transdermally, or orally.

According to another embodiment, the present invention may feature a method of treating a depressive disorder in a subject in need of such treatment. In some embodiments, the method may comprise administering to the subject a therapeutically effective amount of a composition comprising:

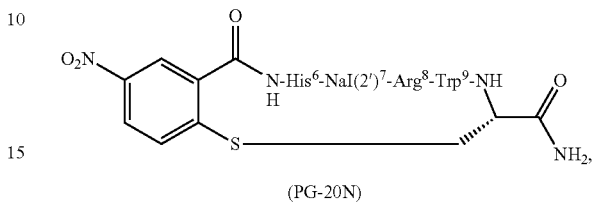

(PG-20N)

in a pharmaceutically acceptable carrier. Preferably, administration of the composition can treat the depressive disorder in the subject such that clinical improvement is observed in about 1 to 14 days. For example, clinical improvement may be observed in about 1-7 days or about 7-14 days.

In some embodiments, the subject may be a mammal, such as a human. In other embodiments, the composition is administered in a dosage of about 0.001 mg/kg to 100 mg/kg of body weight. In one embodiment, the composition may be administered once daily or twice daily. In another embodiment, the composition may be administered at least once daily, at least once every other day, or at least once weekly. In still other embodiments, the composition may be administered intravenously, transdermally, or orally.

In yet another embodiment, the present invention features a composition for use in treating a depressive disorder or an anxiety disorder. The composition for use may comprise:

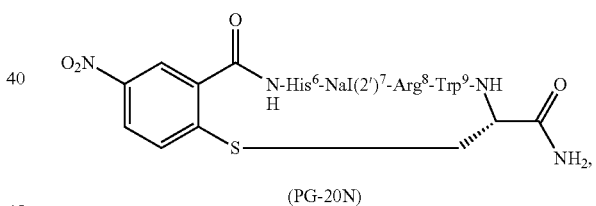

(PG-20N)

in a pharmaceutically acceptable carrier.

In a preferred embodiment, the composition for use is administered to a subject who has been diagnosed with the depressive disorder or the anxiety disorder.

In some embodiments, the composition for use may be administered once daily or twice daily. In another embodiment, the composition may be administered at least once daily, at least once every other day, or at least once weekly. In other embodiments, the composition is administered at a daily dose ranging from about 0.001 mg/kg to 100 mg/kg of body weight. Further still, the composition may be administered intravenously, transdermally, or orally. In preferred embodiments, the composition for use in the treatment resulted in clinical improvement of the depressive disorder or anxiety disorder that is observed in about 1 to 14 days. For example, clinical improvement may be observed in about 1 to 7 days or about 7 to 14 days.

In yet a further embodiment, the present invention features a composition for use in treating a depressive disorder or an anxiety disorder in a subject, comprising determining if the subject has the depressive disorder or the anxiety disorder, and administering a therapeutically effective amount of the composition to the subject if it is determined that the subject has the depressive disorder or the anxiety disorder. The composition for use may comprise:

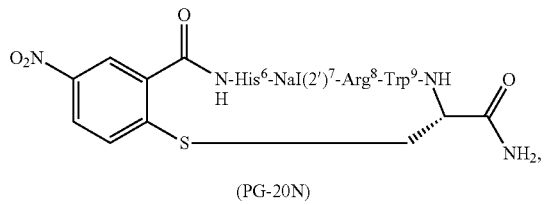

(PG-20N)

in a pharmaceutically acceptable carrier.

In one embodiment, the composition for use may be administered once daily or twice daily. In another embodiment, the composition may be administered at least once daily, at least once every other day, or at least once weekly. In some embodiments, the composition is administered at a daily dose ranging from about 0.001 mg/kg to 100 mg/kg of body weight. In other embodiments, the composition may be administered intravenously, transdermally, or orally. In preferred embodiments, the composition for use in the treatment resulted in clinical improvement of the depressive disorder or anxiety disorder that is observed in about 1 to 14 days. For example, clinical improvement may be observed in about 1 to 7 days or about 7 to 14 days.

In any of the aforementioned embodiments of the present invention, the composition may be administered in a dosage of about 0.001 mg/kg to 100 mg/kg of body weight. For example, the dosage may range from about 0.001 mg/kg to 1 mg/kg of body weight, or about 1 mg/kg to 10 mg/kg of body weight, or about 10 mg/kg to 20 mg/kg of body weight, or about 20 mg/kg to 30 mg/kg of body weight, or about 30 mg/kg to 40 mg/kg of body weight, or about 50 mg/kg to 60 mg/kg of body weight, or about 60 mg/kg to 70 mg/kg of body weight, or about 70 mg/kg to 80 mg/kg of body weight, or about 80 mg/kg to 90 mg/kg of body weight, or about 90 mg/kg to 100 mg/kg of body weight.

Examples of depressive disorders may include, but are not limited to, major depressive disorders or persistent depressive disorders. Examples of anxiety disorders may include, but are not limited to, generalized anxiety disorders or panic disorders.

Without wishing to limit the invention to a particular theory or mechanism, PG-20N is a selective melanocortin-5 receptor (MC5R) antagonist that can block MC5R, and therefore, PG-20N is potentially therapeutic for treating depression and anxiety. Moreover, PG-20N is faster acting and more potent than existing anti-depressants, such as Prozac or Norpramin.

MC5R of the melanocortin system is a potential target for the development of antidepressants. In the present invention, experiments with mice that have been genetically manipulated to abolish MC5R function showed that these mice exhibit low levels of depression- and anxiety-related behaviors in tests that are widely used to screen new antidepressant drugs. Additionally, when normal mice were injected with drugs to activate MC5R, the MC5R activation mimicked the effects of stress by increasing depression-related behavior. Hence, the use of an MC5R antagonist can have effects similar to that of antidepressants on the behaviors of mice. Testing of mice using treatments with classical antidepressants, such as Prozac, are typically long-term treatments. In the present invention, it was discovered that an MC5R antagonist exerts a therapeutic effect after only short-term treatments. Moreover, mice lacking MC5R are healthy with similar longevity to control mice, and no adverse effects of treatment were found with the MC5R antagonist.

Disclosed are the various compounds, solvents, solutions, carriers, and/or components to be used to prepare the disclosed compositions as well as the compositions themselves to be used within the methods disclosed herein. Also disclosed are the various steps, elements, amounts, routes of administration, symptoms, and/or treatments that are used or observed when performing the disclosed methods, as well as the methods themselves. These and other materials, steps, and/or elements are disclosed herein, and it is understood that when combinations, subsets, interactions, groups, etc. of these materials are disclosed, that while specific reference of each various individual and collective combination and permutation of these compounds may not be explicitly disclosed, each is specifically contemplated and described herein.

As used herein, a major depressive disorder (MDD) is a common disorder of mood and affect characterized by one or more major depressive episodes. These episodes are defined diagnostically using a criteria-based syndrome listed and described in literature as would be known to one of ordinary skill in the art. These episodes are diagnosed in a human patient if the patient has experienced 5 symptoms from a list of 9 symptom categories every day, or nearly every day, for a period lasting at least 2 weeks. At least one symptom must be present from either category 1 (having a sad, depressed, empty, or irritable mood, or appearing sad to others), or category 2 (experiencing loss of interest in or pleasure from activities). The other symptom categories include: 3) change in weight and/or appetite, 4) insomnia or hypersomnia, 5) psychomotor agitation or retardation, 6) fatigue and/or loss of energy, 7) feelings of worthlessness and/or excessive or inappropriate guilt, 8) diminished ability to think or of concentrate and/or indecisiveness, and 9) recurrent thoughts of death or suicide.

Persistent depressive disorder, also known as dysthymia, is a chronic (ongoing) type of depression in which a person's moods are regularly low. However, the symptoms are not as severe as with major depression.

Bipolar Disorder (also known as "manic-depressive illness") is a mood disorder arising in a human patient who experiences major depressive episodes which alternate with episodes of mania (in the case of type I) or hypomania (in the case of type II). Mania is a syndrome characterized by a euphoric, expansive, or irritable mood lasting at least one week. In addition, at least three of the following symptoms persisted during the same time period: inflated self esteem and/or grandiosity, decreased need for sleep, increased volume or rate of speech, flight of ideas and/or racing thoughts, distractibility, increased goal-directed activity and/or psychomotor agitation, excessive involvement in pleasurable activities that have a high potential for painful consequences. Mania and hypomania have similar signs and symptoms but are distinguished by the degree to which they result in impaired social and occupational functioning.

Bipolar affective disorder is characterized by two or more episodes in which the patient's mood and activity levels are significantly disturbed, this disturbance consisting on some occasions of an elevation of mood and increased energy and activity (hypomania or mania) and on others of a lowering of mood and decreased energy and activity (depression). Repeated episodes of hypomania or mania only are classified as bipolar. This includes manic depressive illness, psychosis, and reaction. This excludes bipolar disorder, single manic episode and cyclothymia.

In Bipolar affective disorder, current episode mild or moderate depression, the patient is currently depressed, as in a depressive episode of either mild or moderate severity, and has had at least one authenticated hypomanic, manic, or mixed affective episode in the past.

In Bipolar affective disorder, current episode severe depression without psychotic symptoms, the patient is currently depressed, as in severe depressive episode without psychotic symptoms, and has had at least one authenticated hypomanic, manic, or mixed affective episode in the past.

Treatment-resistant depression is exemplified by a case in which a human patient with either major depressive disorder or bipolar disorder continues to meet criteria for a major depressive episode in spite of treatment with conventional antidepressant drugs at adequate doses and treatment durations (at least 4 to 8 weeks).

Panic Disorder is an episodic paroxysmal anxiety syndrome characterized by recurrent attacks of severe anxiety (panic) which are not restricted to any particular situation or set of circumstances and are therefore unpredictable. The symptoms include sudden onset of palpitations, chest pain, dyspnea, dizziness, and feelings of unreality (depersonalization or derealization). There is often also a secondary fear of dying, losing control, or going insane. Panic disorder may be seen with or without agoraphobia, which is characterized by a cluster of phobias embracing fears of leaving home, entering shops, crowds and public places, or traveling alone in trains, buses or planes. Avoidance of the phobic situation is prominent, to an extent that agoraphobics alter their lifestyles to avoid their relevant phobic situations.

Social phobia (also called Social Anxiety Disorder) is characterized by a marked and persistent fear of one or more social or performance settings in which the patient is exposed to unfamiliar people or to possible scrutiny by other people. The patient fears that in such situation they will act in a way (or show anxiety symptoms) that will be humiliating or embarrassing. Exposure to the feared social situation almost invariably provokes anxiety, and this response may progress to panic attacks. The feared social or performance situations are avoided, or else are endured with intense anxiety and distress.

Stress is any uncomfortable emotional experience uncomfortable emotional experience in response to any demand, accompanied by predictable biochemical, physiological and behavioral changes. Stress is often described as a feeling of being overwhelmed, worried or run-down, which can lead to both physical and psychological health issues. Excessive chronic stress, which is constant and persists over an extended period of time, can have health consequences and adversely affect the immune, cardiovascular, neuroendocrine and central nervous systems. Chronic stress can occur in response to everyday stressors that are ignored or poorly managed, as well as to exposure to traumatic events, such as acute stress disorder (ASD) or post-traumatic stress disorder (PTSD). Furthermore, chronic stress can cause or exacerbate health problems such as anxiety and depression, particularly when the stress is not properly managed.

Post-traumatic stress disorder arises as a delayed or protracted response to a stressful event or situation (of either brief or long duration) of an exceptionally threatening or catastrophic nature which is likely to cause pervasive distress in almost anyone. Predisposing factors, such as personality traits or previous history of mood or anxiety disorders, may lower the threshold for the development of the syndrome or aggravate its course, but they are neither necessary nor sufficient to explain its occurrence. Typical features include episodes of repeated reliving of the trauma in intrusive memories ("flashbacks"), dreams or nightmares occurring against the persisting background of a sense of "numbness" and emotional blunting, detachment from other people, unresponsiveness to surroundings, anhedonia, and avoidance of activities and situations reminiscent of the trauma. There often is a state of autonomic hyperarousal with hypervigilance, an enhanced startle reaction, and insomnia. Anxiety and depression commonly are associated with these symptoms and signs. The onset follows the trauma with a latency period that may range from a few weeks to months.

Generalized anxiety disorder is a chronic anxiety syndrome characterized by excessive worry or anxiety over a period lasting at least 6 months. These symptoms are associated with at least 3 of the following 6 symptoms: 1) restlessness or feeling on edge, 2) feeling easily fatigued, 3) impaired concentration, 4) irritability, 5) muscle tension, and 6) sleep disturbance. These anxiety symptoms are generalized and persistent but not restricted to, or even strongly predominating in, any particular environmental circumstances. The anxiety syndrome is sufficiently severe to cause clinically significant distress or to impair social or occupational functioning.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

The terms "administering" and "administration" refer to methods of providing a pharmaceutical preparation to a subject. Such methods are well known to those skilled in the art and include, but are not limited to, administering the compositions orally, parenterally (e.g., intravenously and subcutaneously), by intramuscular injection, by intraperitoneal injection, intrathecally, transdermally, extracorporeally, topically or the like.

A composition can also be administered by topical intranasal administration (intranasally) or administration by inhalant. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering a composition comprising PG-20N, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, for example, U.S. Pat. No. 3,610,795, which is incorporated by reference herein.

A "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of the composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi-permeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. A preferred mode of administration of the composition is orally. Other modes of administration may be topically (including ophthahnically, vaginally, rectally, intranasally), by inhalation, or parenterally, for example by intravenous drip, subcutaneous, intraperitoneal or intramuscular injection. The disclosed compounds can be administered orally, intravenously, intraperitoneally, intramuscularly, subcutaneously, intracavity, or transdermally.

Pharmaceutical compositions for oral administration include, but are not limited to, powders or granules, suspensions or solutions in water or non-aqueous media, capsules, sachets, or tablets. Thickeners, flavorings, diluents, emulsifiers, dispersing aids or binders may be desirable. The composition of PG-20N can be administered to a subject orally in a dosage taken once daily or in divided doses. The medication can be administered for one day and then stopped if clinical improvement occurs rapidly. Furthermore, the medication can be administered as infrequently as once every 4 to 8 weeks. A person of skill, monitoring a subject's clinical response, can adjust the frequency of administration of the medication according to methods known in the art.

Preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like may be necessary or desirable.

In one aspect, PG-20N can be administered in an intravenous dosage. This dosage can be administered to a subject once daily or in divided dosages throughout a day, as determined by methods known in the art. This dosage can be administered to a subject for one day and then stopped if the subject responds immediately, or the dosage can be administered on a daily basis until a clinical response is noted. It is contemplated that the dosage of PG-20N can be administered as infrequently as once every month or every two months, or at any interval in between, depending on a subject's clinical response to the medication. Thus, if a subject responds to one dosage of PG-20N, a person of skill may determine that further dosages of the medication can be withheld. Moreover, if a subject does not respond to the initial dosage and administration of PG-20N, a person of skill can administer the medication daily for several days until such response occurs. A person of skill can monitor a subject's clinical response to the administration of PG-20N, and administer additional dosages if the subject's mood disorder symptoms reappear after a period of remission. It is contemplated that PG-20N, can be administered to a subject with, for example, major mood disorder on a twice daily basis, once daily basis, on an alternating daily basis, on a weekly basis, on a monthly basis, or at any interval in between.

In another aspect, PG-20N can be administered to a subject transdermally, by using an adherent patch, by using iontophoresis, or by using any other method known to a person of skill. The dosage of PG-20N, administered transdermally can be given daily or infrequently as once every week or every 2-8 weeks. A person of skill, monitoring a subject's clinical response and improvement, can determine the frequency of administration of the medication by methods known in the art.

In another aspect, PG-20N can be administered to a subject intranasally in a dosage taken once daily or in divided doses. The medication can be administered for one day and then stopped if clinical improvement occurs rapidly. Further, the medication can be administered as infrequently as once every 4 to 8 weeks. A person of skill, monitoring a subject's clinical response to the administration of the medication, can adjust the frequency of administration according to methods known in the art.

In another aspect, PG-20N can be administered to a subject intramuscularly in a dosage taken once daily or in divided doses. The medication can be administered for one day and then stopped if clinical improvement occurs rapidly. Furthermore, the medication can be administered as infrequently as once every 4 to 8 weeks. A person of skill, monitoring a subject's clinical response, can adjust the frequency of administration of the medication according to methods known in the art.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

```
                      SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: synthetic melanocortin 5 receptor (MC5R)
      peptide
<220> FEATURE:
<221> NAME/KEY: MISC_FEATURE
<222> LOCATION: (1)..(5)
<223> OTHER INFORMATION: Cyclization via S in side chain of Cys linked
      to C7H4NO4 that is linked to amine at the N-terminal in His
<220> FEATURE:
<221> NAME/KEY: MISC_FEATURE
<222> LOCATION: (2)..(2)
<223> OTHER INFORMATION: L-Nal(2')

<400> SEQUENCE: 1

His Xaa Arg Trp Cys
1               5
```

What is claimed is:

1. A method of treating a depressive disorder or an anxiety disorder in a subject in need of such treatment, said method comprising administering to the subject a therapeutically effective amount of a composition comprising:

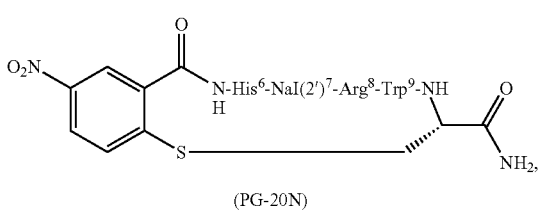

(PG-20N)

in a pharmaceutically acceptable carrier.

2. The method of claim 1, wherein the subject is a mammal.

3. The method of claim 2, wherein the mammal is a human.

4. The method of claim 1, wherein the composition is administered in a dosage of about 0.001 mg/kg to 100 mg/kg of body weight.

5. The method of claim 1, wherein the composition is administered at least once daily, at least once every other day, or at least once weekly.

6. The method of claim 1, wherein the composition is administered intravenously, transdermally, or orally.

7. A method of treating a depressive disorder in a subject in need of such treatment, said method comprising administering to the subject a therapeutically effective amount of a composition comprising:

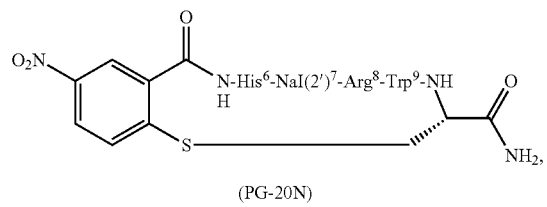

(PG-20N)

in a pharmaceutically acceptable carrier, wherein administration of the composition treats the depressive disorder in the subject such that clinical improvement is observed in about 1 to 14 days.

8. The method of claim 7, wherein the subject is a mammal.

9. The method of claim 8, wherein the mammal is a human.

10. The method of claim 7, wherein the composition is administered in a dosage of about 0.001 mg/kg to 100 mg/kg of body weight.

11. The method of claim 7, wherein the composition is administered at least once daily, at least once every other day, or at least once weekly.

12. The method of claim 7, wherein the composition is administered intravenously, transdermally, or orally.

* * * * *